US 9,144,450 B2

(12) United States Patent
Newell et al.

(10) Patent No.: US 9,144,450 B2
(45) Date of Patent: Sep. 29, 2015

(54) FLUID SEALANT COMPOSITIONS AND VARIOUS MEDICAL APPLICATIONS PERTAINING TO THE SAME

(75) Inventors: Kevin L. Newell, Jefferson, MA (US); Christopher Oskin, Grafton, MA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 794 days.

(21) Appl. No.: 13/315,547

(22) Filed: Dec. 9, 2011

(65) Prior Publication Data

US 2012/0165804 A1 Jun. 28, 2012

Related U.S. Application Data

(60) Provisional application No. 61/426,361, filed on Dec. 22, 2010.

(51) Int. Cl.
*A61B 18/04* (2006.01)
*A61B 18/00* (2006.01)

(52) U.S. Cl.
CPC ....... *A61B 18/04* (2013.01); *A61B 2018/00035* (2013.01); *A61B 2018/00559* (2013.01)

(58) Field of Classification Search
CPC .............. A61B 18/04; A61B 2018/00035; A61B 2018/00559
USPC ........................................................ 606/27
See application file for complete search history.

(56) References Cited

U.S. PATENT DOCUMENTS

| 6,689,103 B1 * | 2/2004 | Palasis ........................ 604/173 |
| 2006/0206209 A1 * | 9/2006 | Cragg et al. ............... 623/17.16 |
| 2008/0004662 A1 * | 1/2008 | Peters et al. ..................... 607/3 |
| 2008/0097563 A1 * | 4/2008 | Petrie et al. .................. 607/105 |
| 2008/0208163 A1 * | 8/2008 | Wilkie ......................... 604/506 |
| 2009/0069796 A1 * | 3/2009 | Oskin ........................... 606/27 |
| 2009/0148502 A1 * | 6/2009 | Pronovost ................... 424/447 |

OTHER PUBLICATIONS

Suzuki et al., "Phase transition in polymer gels induced by visible light", Nature, vol. 346, Jul. 26, 1990, pp. 345-347.
Hydro ThermAblator® System (HTA® System), 2pp, Downloaded Apr. 22, 2010 from http://wwwbostonscientific.com.
"HTA ProCerva™ Procedure Sheath and the HTA® System", Mar. 2009, 4pp.
"Hydro ThermAblator® (HTA) System: Requires no uterine manipulation, provides direct visualization", Supplement to OBG Management, Dec. 2009, S6-S10.

* cited by examiner

*Primary Examiner* — Carl H Layno
*Assistant Examiner* — Erin Piateski
(74) *Attorney, Agent, or Firm* — Fay Kaplun & Marcin, LLP (57) ABSTRACT

The present description relates to fluid sealant compositions that increase in viscosity upon administration to a subject, to medical procedures employing such compositions, to methods for administering such compositions, and to products containing such compositions including medical devices, medical device components and kits, among other aspects.

13 Claims, 8 Drawing Sheets

FLUID SEALANT COMPOSITIONS AND VARIOUS MEDICAL APPLICATIONS PERTAINING TO THE SAME

RELATED APPLICATION SECTION

This application claims the benefit of U.S. Provisional Patent Application Ser. No. 61/426,361, filed Dec. 22, 2010, entitled "FLUID SEALANT COMPOSITIONS AND VARIOUS MEDICAL APPLICATIONS PERTAINING TO THE SAME," which is incorporated by reference herein in its entirety.

FIELD OF THE INVENTION

The present description relates to fluid sealant compositions that increase in viscosity upon administration to a subject, to medical procedures employing such compositions, to methods for administering such compositions, and to products containing such compositions, including medical devices, medical device components, and kits, among other aspects.

BACKGROUND

A wide variety of medical procedures are conducted in which it is desirable to form a barrier between a treatment site and an adjacent site. For instance, hydrothermal endometrial ablation (HTA) is used to treat women who experience abnormal uterine bleeding. During the procedure, a doctor typically uses an HTA console and delivery device (introducer) to deliver heated saline into the uterus of the patient to destroy the inner lining of the uterus. During the procedure, a seal is formed between the uterus and the vagina to prevent heated fluid from migrating from the uterus to the vagina, which can cause discomfort.

SUMMARY OF THE INVENTION

In one aspect, the present disclosure pertains to fluid sealant compositions, including thermoresponsive fluid sealants, which increase in viscosity upon administration to a subject.

In another aspect, the present disclosure pertains to medical procedures in which such fluid sealant compositions are used to isolate one part of the body from another during the course of the medical procedure. One exemplary embodiment of such a procedure is a heated fluid ablation procedure in which a thermoresponsive fluid sealant is used to isolate to isolate one part of the body (e.g., uterus, etc.) from another part (e.g., vagina, ovary, etc.) during the course of procedure.

In another aspect, the present disclosure pertains to kits that comprise containers containing such fluid sealant compositions as well as instructions regarding how to use such compositions in one or more medical procedures. For example, in one exemplary embodiment, the present disclosure pertains to kits that comprise a thermoresponsive fluid sealant in a container and instructions regarding the use of the sealant composition in conjunction with a heated fluid ablation procedure.

In another aspect, the present disclosure pertains to medical devices and medical device components that are used to administer such fluid sealant compositions. Exemplary embodiments include pumps, reservoirs, cassettes, introducers, and so forth, for use in medical procedures employing such compositions.

These and many other aspects and embodiments will become readily apparent to those of ordinary skill in the art upon review of the Detailed Description and any claims to follow.

DETAILED DESCRIPTION

A more complete understanding of the present invention is available by reference to the following detailed description of various aspects and embodiments of the invention. The detailed description of the invention which follows is intended to illustrate but not limit the invention. The scope of the invention is defined by any appended claims.

The present description relates to fluid sealant compositions (also referred to herein as "fluid sealants" and "sealant fluids") that increase in viscosity upon administration to a subject, to medical procedures employing such compositions, to methods for administering such compositions, and to products containing such compositions including medical devices, medical device components and kits, among other aspects.

As used herein, "subjects" are vertebrate subjects, more typically mammalian subjects, including human subjects, pets and livestock.

A composition is "fluid" at a given temperature if it has the ability to flow when subjected to a shear stress. A fluid will assume the shape of its container over time. Such compositions include, for example, free flowing liquid compositions as well as viscous, gel-like materials at that may be delivered to a desired site by injection (e.g., through a syringe, catheter, and so forth).

Such fluid sealant compositions may undergo an increase in viscosity, for instance, as a result of a change in environment at the administration site, for example, as a result of a change a change in temperature, pH, pressure or light level (e.g., infrared, ultraviolet, visible), or as a result of a chemical or biological reaction (e.g., a crosslinking reaction).

In certain embodiments, fluid sealant compositions include those that increase in viscosity when cooled to body temperature (e.g., ~37° C. for humans) from a temperature above body temperature (e.g., 40° C. to 45° C. to 50° C. or more). In certain embodiments, such compositions reversibly decrease in viscosity when subsequently heated from body temperature back to a temperature above body temperature (which temperature will depend on the nature of the fluid sealant composition).

In certain embodiments, fluid sealant compositions include those that increase in viscosity when warmed to body temperature (e.g., ~37° C. for humans) from a temperature below body temperature (e.g., 35° C. to 30° C. to 25° C. to 20° C. to 15° C. or less, including typical room temperatures of 20° C. to 30° C. (68° F. to 86° F.)). In certain embodiments, such compositions reversibly decrease in viscosity when subsequently cooled from body temperature back to a temperature below body temperature (which temperature will depend on the nature of the fluid sealant composition).

For example, in certain embodiments, such thermoresponsive fluid sealant compositions are injected into the body at a temperature below body temperature. As the composition equilibrates with the temperature of the body, the viscosity of the composition increases. In preferred embodiments, a fluid sealant composition may be selected that increases in viscosity (e.g., an increase of five-fold or more, ten-fold or more, twenty-fold or more, one-hundred-fold or more, or even one-thousand-fold or more, among other possibilities) as the temperature rises to the body temperature of the subject from an introduction temperature that lies in a range from 15° C. to 20° C. to 25° C. to 30° C. to 35° C., more preferably an introduction temperature that ranges from 20° C. to 25° C.

Conversely, at a later time (e.g., after conducting a medical procedure), the temperature of the gel may be reduced to below body temperature using a suitable technique, thereby rendering the sealant fluid composition less viscous and thus more easily removed from the body. For instance, the composition may be exposed to cold water or saline (e.g., using a catheter), which in addition to reducing the viscosity of the composition may also have the effect of dissolving the gel.

Beneficial fluid sealant compositions of this type include compositions that comprise so-called reverse thermosensitive polymers. For example, in certain embodiments, a polymer solution (e.g., an aqueous or organic solution) containing of one or more reverse thermosensitive polymers may be employed as a fluid sealant composition. These polymer solutions are liquids below body temperature and viscous gels at body temperature. In various embodiments, the polymer solution is provided external of the body at a temperature below body temperature. The polymer solution may be further chilled to prolong the time the gel stays in the liquid form upon introduction into the body, in some embodiments. For example, the introduction temperature may be is about 10° C. below the gelation temperature of the polymer solution.

Reverse thermosensitive polymers may be characterized in accordance with ASTM D-5133, which is incorporated by reference herein in its entirety. The measurements resulting from this test method are viscosity, the maximum rate of viscosity increase (the gelation index), and the temperature at which the gelation index occurs (the gelation temperature). Preferred gelation temperatures range from 30 to 37° C., among other possibilities.

In certain embodiments, the reverse thermosensitive polymer employed may be a block copolymer. The block copolymer may be a biodegradable, biocompatible block copolymer that comprises a polyoxyalkylene block, for example, a block copolymer comprising polyoxyethylene, blocks, polyoxypropylene blocks, or both polyoxyethylene and polyoxypropylene blocks.

In certain embodiments, the block copolymers employed have a number-average molecular weight (Mn) ranging from about 1,000 to 500,000 Daltons or more, for instance, from 1,000 to 2,000 to 5,000 to 10,000 to 20,000 to 50,000 to 100,000 to 200,000 to 500,000 Daltons or more. In certain embodiments, the polymer is in an aqueous solution. For example, aqueous solutions may contain about 5% to about 30% polymer, more typically about 10% to about 25% polymer.

The pH of reverse thermosensitive polymer solutions may vary widely, but preferably range from about 6.0 to about 7.8, which are suitable pH levels for injection into a mammalian body.

In certain embodiments, the reverse thermosensitive polymers used are poloxamers or poloxamines. Polymers of this type are also referred to as reversibly gelling, and their viscosity increases and decreases with an increase and decrease in temperature, respectively. Several members of this class of polymer, including poloxamer 188, poloxamer 407, poloxamer 338, poloxamine 1107 and poloxamine 1307, show reverse thermosensitivity at or near the physiological temperature range. These polymers are members of a class that are soluble in aqueous solutions at low temperature, but which form gels at higher temperatures. For instance, poloxamer 407 is a biocompatible polyoxypropylene-polyoxyethylene block copolymer having an average molecular weight of about 12,500 and a polyoxypropylene fraction of about 30%, whereas poloxamer 188 has an average molecular weight of about 8400 and a polyoxypropylene fraction of about 20%, poloxamer 338 (Pluronic™ F108) has an average molecular weight of about 14,600 and a polyoxypropylene fraction of about 20%, poloxamine 1107 has an average molecular weight of about 14,000 and poloxamine 1307 has an average molecular weight of about 18,000.

Polyoxypropylene-polyoxyethylene block copolymers that have these properties include polymers that are available commercially as Pluronic™ poloxamers and Tetronic™ poloxamines (BASF, Ludwigshafen, Germany) and generically known as poloxamers and poloxamines, respectively. Pluronic™ polymers have surfactant abilities and low toxicity and immunogenic responses. A specific example of such a polymer is described in Example of Pub. No. US 2008/0208163 to Wilkie, wherein LeGoo™ (poloxamer 407) at 20% aqueous concentration is used to close a femoral arteries of pigs.

For further information regarding reverse thermosensitive polymers, methods of purifying the same, and methods of modifying the transition temperature of the same, among other information, see US 2008/0208163 to Wilkie.

In addition to agents that are responsible for increasing viscosity of the fluid sealant compositions on application to a subject, fluid sealant compositions in accordance with the present disclosure may further a number of supplemental agents. For example, therapeutic agents and/or contrast-enhancing agents may be added to the compositions in some embodiments.

In this regard, in certain embodiments, to aid in visualization, a contrast-enhancing agent can be added to the fluid sealant compositions described herein. Exemplarily contrast-enhancing agents are radiopaque materials, paramagnetic materials, heavy atoms, transition metals, lanthanides, actinides, dyes, and radionuclide-containing materials.

In certain embodiments, therapeutic agents, including a non-steroidal anti-inflammatory agents, steroids, analgesics and an antimicrobial agents, among others may be added to the fluid sealant compositions described herein.

In various embodiments, fluid sealant compositions like those described herein are used to isolate one part of the body from another part of the body during a medical procedure.

Although fluid sealant compositions that increase in viscosity upon administration to a subject are preferred as described herein, as will be appreciated by those of ordinary skill in the art, in certain embodiments, fluid sealant compositions (e.g., gels, etc.) may be employed which are sufficiently viscous at the delivery temperature to isolate one part of the body from another part of the body during a medical procedure. (Due to their viscosities, such compositions may require higher pressures to deliver them than the temperature sensitive sealants described elsewhere herein.) After the medical procedure has been conducted, such compositions may be removed, for example, by flushing with a suitable fluid (e.g., water, saline, etc.). For this purpose, water-soluble fluid sealant compositions may be preferred.

For example, such compositions may be used to block particle migration of polyps or tumor migration during laser treatment in an anatomic lumen wherein it is desirable to restrict movement of tissue, debris, and so forth, during a procedure. As another example, such fluid sealant compositions can be used within the ear or nasal passages during surgery to protect foreign bodies from going into the body during the procedure. As another example, such compositions may be used during laparoscopic surgery to close off surgery sites to prevent migration of debris during the surgery.

As yet another example, such compositions may be used during a heated fluid ablation procedure to ensure that the hot fluid remains within a hollow organ being treated (e.g., a uterus) and does not contact adjacent tissues/organs or exit the body during the procedure. For example, such compositions may be used during a heated fluid ablation procedure to ensure that the hot fluid remains within the uterus and does not travel into the vagina and/or into the fallopian tubes during the procedure.

Such compositions may be applied using a suitable delivery system, for example, one comprising a suitable application device, for instance, an elongate member with one or more lumens (e.g., catheter, introducer sheath, cannula, etc.) in fluid communication with a reservoir containing the fluid sealant composition and a system for pumping the fluid composition from the reservoir, through the elongate member and into a subject.

Examples of pumps which may be employed for this purpose include positive displacement pumps such as rotary-type positive displacement pumps and reciprocating-type positive displacement pumps, for instance, rotary lobe pumps, progressing cavity pumps, rotary gear pumps, screw pumps, gear pumps, roots-type pumps, hydraulic pumps, vane pumps, regenerative (peripheral) pumps, peristaltic pumps, piston pumps, syringe pumps, and diaphragm pumps, velocity pumps, for instance, centrifugal pumps, radial flow pumps, axial flow pumps, mixed flow pumps and eductor-jet pumps, as well as buoyancy pumps, impulse pumps and gravity pumps, among others.

In one specific embodiment, a syringe pump is employed for this purpose.

In certain embodiments, fluid compositions for use in accordance with the present disclosure (e.g., fluid sealant compositions, thermal ablation fluids, etc.) are pumped from a console with an insertable and removable cassette, which may later be disposable after use in some embodiments. The cassette may contain, for example, entire pumps or may contain pump drive mechanisms (e.g., impellers, pistons, gears, vanes, screws, diaphragms, etc.) which are coupled (e.g., mechanically, magnetically, etc.) to a source of power (e.g., motor, etc.) outside the cassette (e.g., within the console).

Delivery systems for administering fluid sealant compositions may further include a mechanism for cooling the fluid sealant composition before delivering the same to a subject. For example, the delivery system may include a refrigeration device or one or more so-called "cold-packs" for cooling the fluid sealant composition within the reservoir. Cold packs contain two containers containing chemicals separated by a seal. When the seal is broken, as the contents from the separate containers begin to react, energy is absorbed from the surroundings creating a cooling effect.

Delivery systems for administering fluid sealant compositions may be integrated with a system for performing a related procedure (e.g., thermal ablation procedure, colonoscopy, laparoscopic surgery, etc.) or it may be a stand-alone system.

In some embodiments, a fluid sealant composition is provided in conjunction with a medical kit. For instance, a kit may be supplied which comprises a fluid sealant composition within a container and instructions regarding the use of the sealant composition in conjunction with a medical procedure. For example, the medical procedure may be a thermal ablation procedure and/the container may be syringe which is adapted for use with a syringe pump.

The discussion to follow will be based on an exemplary embodiment of a system for use in thermal ablation procedures. However, the present disclosure is clearly not so-limited.

Described is a method of conducting a fluid thermal ablation procedure in a uterus of a female subject. The procedure comprises first introducing a sheath into the uterus of the subject through the endocervical canal of the cervix. Then, a seal is formed between the sheath and the endocervical canal by applying a thermoresponsive sealant fluid (e.g., one comprising an aqueous solution of a polymer, among many other possibilities) between the sheath and the cervix within the endocervical canal. After the seal is formed, heated fluid is introduced into the uterus through the sheath to ablate the ureteral lining. In some embodiments, a catheter is employed apply the thermoresponsive sealant fluid to the openings to the fallopian tubes. Current thermal ablation systems require that the system pressure stay below the pressure required to open the fallopian tubes. By sealing the fallopian tubes, however, a higher system pressure can be maintained.

Figure 1:
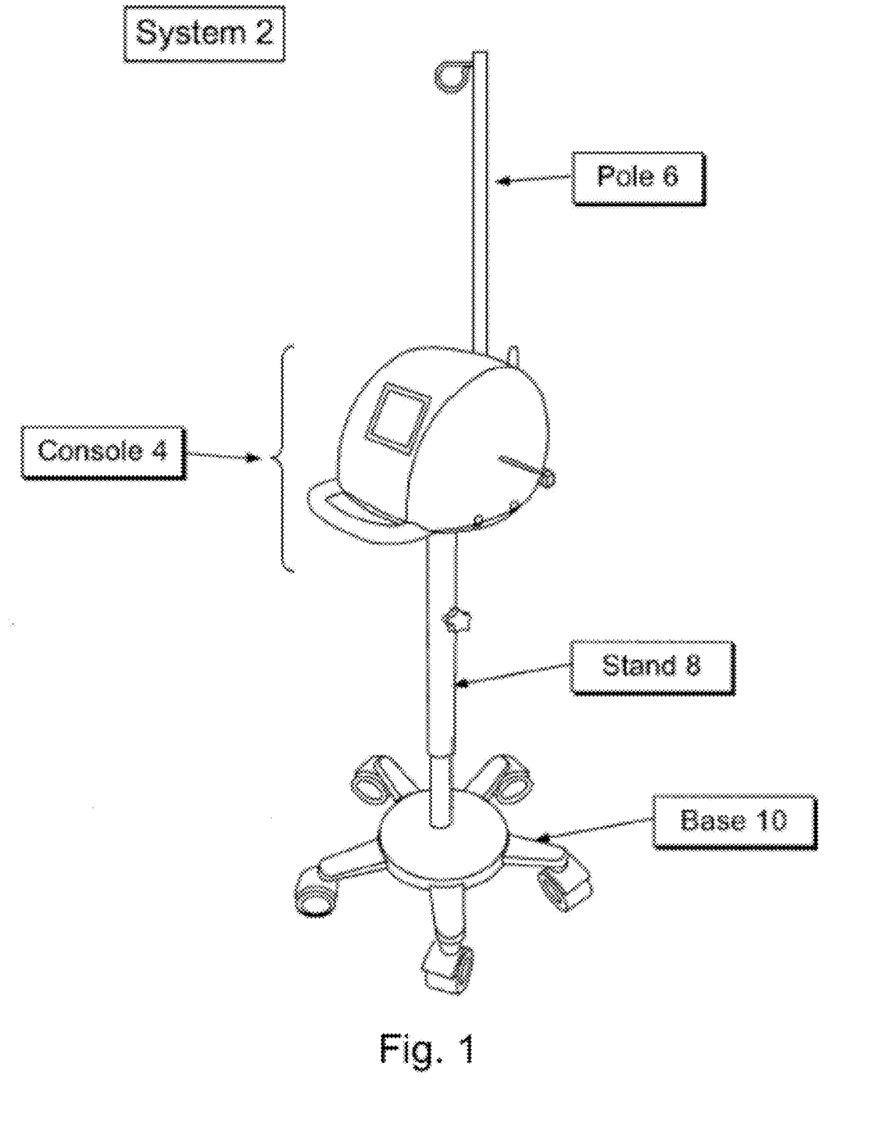
FIG. 1 shows an exemplary embodiment of a thermal ablation system according to the present disclosure.

FIG. 1 shows an exemplary embodiment of a thermal ablation system 2 according to the present disclosure. Generally, the system 2 includes a console 4 having a pole 6 extending from an upper portion thereof and a stand 8 coupled to a lower portion thereof. The pole 6 preferably extends to a predetermined height above the console 4 so that an intravenous (IV) bag (not shown) hung therefrom will supply fluid to the console 4 at a desired pressure. The IV bag contains fluid such as saline that will be heated and circulated through the uterus to ablate the endometrial lining. During the ablation procedure, an operator (e.g., physician, nurse, etc.) may be required to substitute the IV bag for IV bags with other fluids depending on stage of the ablation procedure. For example, prior to the procedure an anesthetic fluid may be circulated through the uterus to numb the surgical site. Additionally, after the endometrial lining has been ablated, an analgesic and/or infection preventative solution may be circulated through the uterus. In another exemplary embodiment, IV bags for any fluids required during the procedure may be concurrently attached to the pole 6 with the height of the pole 6 determining the pressure at which these fluids will be supplied to the console 4. In the exemplary embodiment, the stand 8 is provided with a mobile base 10 (e.g., locking wheels) so that the system 2 is easily moveable and steerable. However, those of skill in the art will understand that the base 10 may be static or that electronic control and movement of the system 2 may also be implemented.

Figure 2:
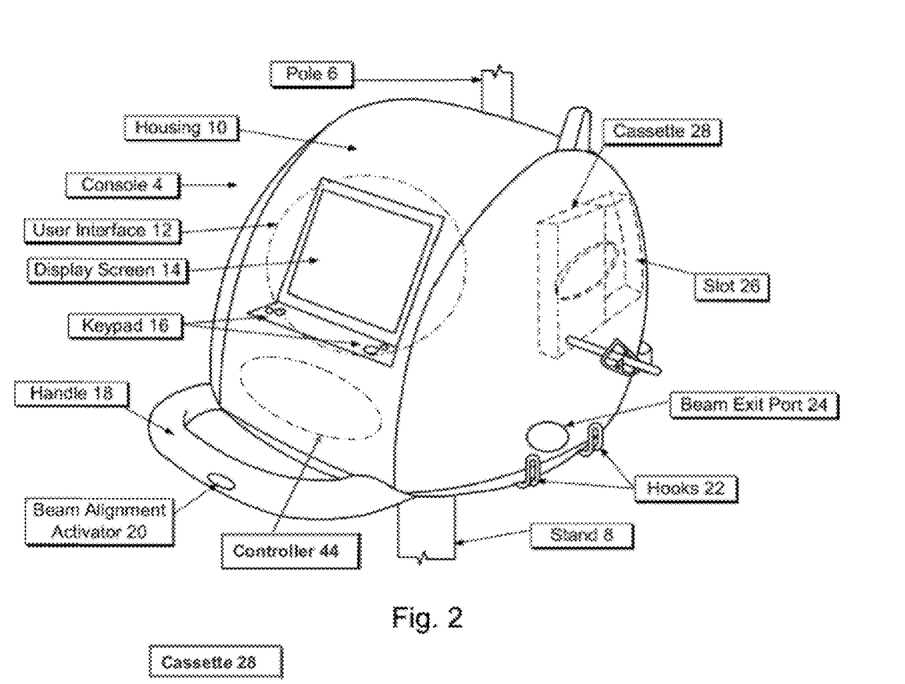
FIG. 2 shows a frontal view of an exemplary embodiment of a console of a thermal ablation system according to the present disclosure.

As shown in FIG. 2, the console 4 according to the present disclosure comprises a housing 10 encasing electronic circuitry and providing a user interface 12 for displaying content (e.g., instructions, procedural data, warnings, etc.) and receiving user input. The user interface 12 may comprise a display screen 14 (e.g., LCD, LED, etc.) and a keypad 16 for submitting input to the console 4. Those of skill in the art will understand that the keypad 16 may be replaced or augmented by mouse, dials, switches, a touch screen (or the screen 14 may be made responsive to tactile input) or any other controls operable by the operator of the system 2. The console 4 also includes a controller 44. The controller 44 may comprise a central processing unit which coordinates operation of the system 2 during the ablation procedure.

The housing 10 may further include a handle 18 for steering the system 2 and a slot 26 receiving a cassette 28, which is described below. In the exemplary embodiment, the handle 18 includes an alignment beam activator 20 which, when pressed, causes a light beam (e.g., laser light) to be emitted from a beam exit port 24 on the console 4. As would be understood by those skilled in the art, the light beam may preferably be oriented horizontally so that, as the height of the console 4 is adjusted using the height adjusting mechanism on the stand 8 until the beam is positioned on a desired portion of the patient's anatomy, the operator will know that the console 4 is in a desired position relative to the uterus. Making the console 4 a desired height off the floor relative to the uterus (e.g., the same height) ensures that a pressure with which the ablation fluid is circulated in the uterus does not exceed a predetermined value. The housing 10 preferably also includes a hook 22 for hanging a drainage bag (not shown) from the console 4. After ablating the endometrial lining, the ablation fluid is discharged into the drainage bag.

Figure 3:
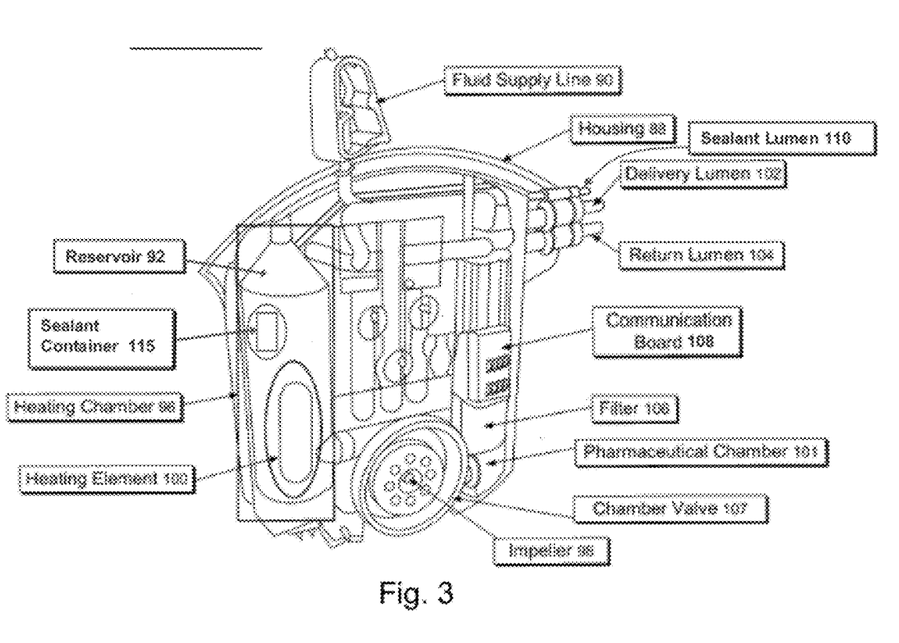
FIG. 3 shows a partial inner view of an exemplary embodiment of a cassette of a thermal ablation system according to the present disclosure.

FIG. 3 shows an exemplary embodiment of the cassette 28 according to the present disclosure. The cassette 28 may be embodied in a housing 88 sized and shaped to fit within the slot 26 on the console 4. For example, the housing 88 may include rails along its sidewalls which are received by guides on the sidewalls of the slot 26, allowing the cassette 28 to slide thereinto. Once in the slot 26, the cassette 28 may be mechanically locked in place (e.g., via latches, hooks, etc.), gravitationally held in the slot 26, magnetically coupled to the console 4, etc. In one exemplary embodiment, the instructions provided on the user interface 12 may instruct the operator on how and when to insert and remove the cassette 28. The console 4 may lock the cassette 28 in the slot 26 to prevent removal during an ablation procedure.

The ablation fluid from the IV bag enters the cassette 28 via a fluid supply line 90 which terminates within a reservoir 92. In this embodiment, a level sensor not shown may be disposed within the reservoir 92 for monitoring a volume of fluid therein. During the ablation procedure, the controller 44 compares the volume to a predetermined volume (or range thereof) to determine whether ablation fluid has been lost/leaked. Based on the results of the comparison, the controller 44 may shut down or execute a predetermined safety procedure. In one exemplary embodiment, the level sensor comprises a plurality of level sensors (e.g., capacitors) arranged along a height of the reservoir. By analyzing signals received from the level sensors, the controller 44 may determine the volume of the fluid within the reservoir 92.

The ablation fluid in the reservoir 92 is directed into a heating chamber 96 by an impeller 98 which is rotated by an impeller coupling not shown in the console 4. For example, current supplied to a motor in the console can be used to rotate an armature thereof which, in turn, rotates the impeller coupling. In one exemplary embodiment, the impeller coupling includes one or more magnets which, when the cassette 28 is inserted into the console 4, are magnetically coupled to one or more magnets on the impeller 98 in the cassette 28 so that rotation of the impeller coupling rotates the impeller 98 to drive fluid through the cassette 28 and into the patient with no contact between ablation fluid in the cassette 28 and components of the console 4 lying outside the cassette 28. Further information on an impeller of this type can be found in Pub. No. 2009/0069796 to Oskin. Those of skill in the art will understand that the motor-coupled impeller is an exemplary embodiment of any power-coupled pump drive mechanism which may be used to output fluid from the cassette 28.

The heating chamber 96 includes a heating element 100 which heats the ablation fluid therein. Operation of the heating element 100 may be based on a temperature measurement of the ablation fluid obtained by a temperature sensor (e.g., thermistor) in the heating chamber 96. By monitoring the temperature measurement, the controller 44 ensures that the ablation fluid temperature is within a predetermined range (e.g., a temperature hot enough to ablate tissue). Those of skill in the art will understand that the heating element 100 may further include a cooling element or be deactivated when, for example, the ablation procedure has been completed and the remaining surface tissue in the uterus is to be allowed to cool.

Introduction of cooled fluid may also be useful in assisting with the removal of thermoresponsive sealant fluid from the cervix and/or fallopian tubes. As noted above, exposure to cold water or saline will reduce the viscosity of the thermoresponsive sealant fluid and can also act to dissolve the same.

When the ablation fluid exits the heating chamber 96 after having reached the desired temperature, it leaves the cassette 28 via a delivery lumen 102 and passes into an introducer which comprises a sheath that is inserted into the uterus via the cervix. The ablation fluid is circulated through the uterus and returned to the cassette 28 via a return lumen 104. The returned ablation fluid is then passed through a filter 106 to remove any tissue remnants, coagulated plasma, etc. and fed back through the impeller 98 into the heating chamber 96. By continuously circulating the returned ablation fluid while monitoring any volumes of ablation fluid added/removed from the system 2, the controller 44 detects any change from the initial ablation fluid volume as described above to determine a volume of ablation fluid absorbed into the body. When the ablation procedure has been completed, the ablation fluid is drained into a drainage bag via a drainage lumen (not shown).

Electrical signals generated by the temperature sensors in the heating chamber 96 and the level sensors in the reservoir 12 are transferred to the controller 44 via a communications circuit board 108 and digitized. The digitized signals are then converted into procedural data (e.g., temperature data and volume data) which is analyzed by the controller 44 to monitor the progress of the ablation procedure.

A therapeutic agent chamber 101 may be formed in the cassette 28 for storing a predetermined volume of a therapeutic agent. The therapeutic agent is retained in the chamber 101 by a chamber valve 107 which is selectively opened and closed by the controller 44 to open and close an output lumen of the chamber 101 in coordination with the ablation procedure. When the chamber valve 107 is open, the therapeutic agent is permitted to flow to the impeller 98 (e.g., by gravity, by suction created by rotation of the impeller 98, by pump, etc.) via the output lumen and be pumped out of the cassette 28 into the uterus. In the exemplary embodiment shown, the therapeutic agent stored in the chamber 101 may be a non-steroidal anti-inflammatory agent, a steroid, an analgesic (e.g., ketorolac tromethamine), an antimicrobial agent, an anesthetic or any combination thereof which may be used to reduce inflammation, discomfort, possibility of infection or other deleterious effect associated with ablating tissue, or any other therapeutic agent. In another exemplary embodiment, an external therapeutic agent source is coupled to the cassette 28 via the fluid supply line 90 instead of or in addition to using the chamber 101.

Cassette 28 further includes a sealant container 115, which contains a fluid sealant composition such as one of those described above. The sealant container 115 is schematically shown within the reservoir 92 in FIG. 3 but could clearly be provided elsewhere in the cassette 28. Prior to introducing ablation fluid, the fluid sealant composition in the sealant container 115 is pumped from the cassette via sealant lumen 110. In the present exemplary embodiment, the fluid sealant composition is pumped via a syringe pump, but one skilled in the art will recognize that other pumping mechanisms are suitable.

Figure 3A:
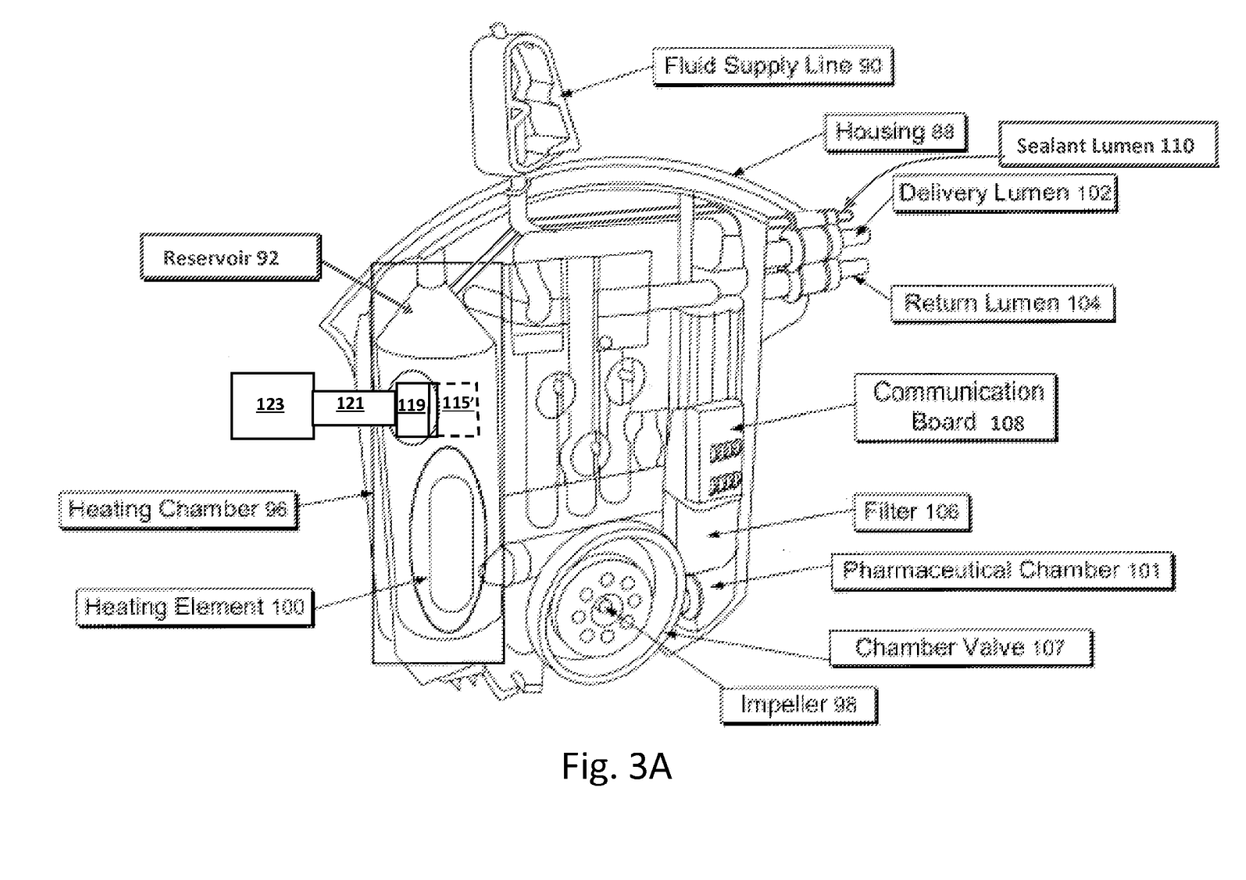
FIG. 3A shows a partial inner view of an exemplary embodiment of a cassette of a thermal ablation system like that of FIG. 3, with additional features illustrated, according to the present disclosure.

In this embodiment, reservoir 92 includes a syringe retainer, and the sealant container 115 corresponds to a syringe 115' which includes barrel that is loaded with the fluid sealant composition and a plunger 119 movably positioned in the barrel for expelling the fluid sealant composition. A motor 123 and power coupler (e.g., a motor-driven actuation rod 121) within the console 4 is positioned to allow the actuation rod 121 to extend into the cassette 28 for engagement with the plunger 119. The controller 44 within the console 4 regulates the rate of movement of the actuation rod 121 (and thus the plunger 119) during delivery of the fluid sealant composition. A monitoring circuit within controller 44 connected to receive signals from a potentiometer and a movable contact associated with the actuation rod 121 may be used to indicate actuation rod 121 movement. As the plunger 119 is urged forward within the syringe barrel by the motor-driven actuation rod 121, the fluid sealant composition is forced from the syringe in the reservoir 92 and exits the cassette 28 through the sealant lumen 110.

Although the pump drive mechanism (i.e., the piston within the syringe barrel) is provided within the cassette, and the motor and power coupler (i.e., the motor-driven actuation rod) are provided outside the cassette in the above exemplary embodiment, this need not be the case. For example, in some embodiments, the motor, power coupler and pump drive mechanism may all be provided within the cassette. In other embodiments, the motor, power coupler and pump drive mechanism may all be provided in the console outside the cassette. In still other embodiments, the motor, power coupler and pump drive mechanism may all be provided outside the console and the cassette (e.g., as part of a stand-alone pumping unit).

Figure 4:
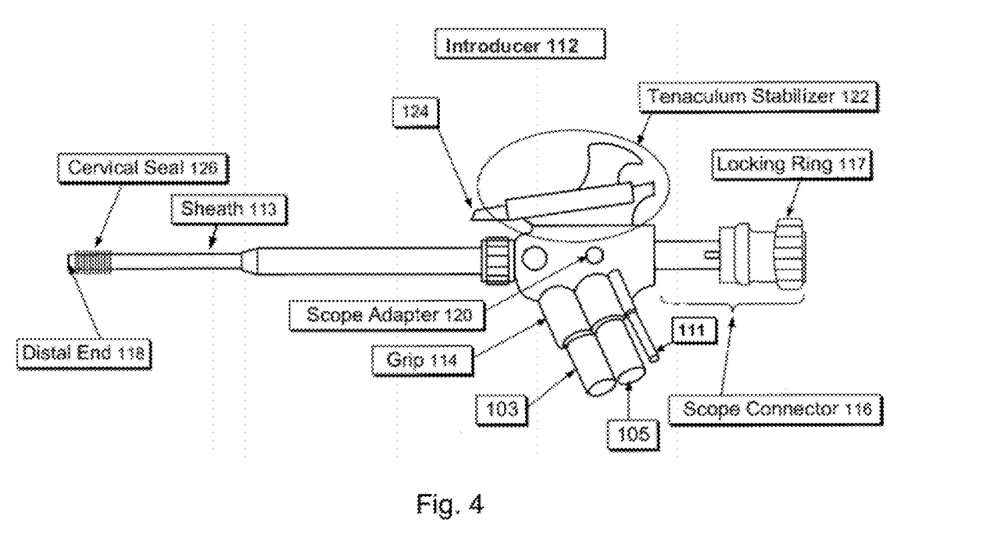
FIG. 4 shows an exemplary embodiment of an introducer of a thermal ablation system according to the present disclosure.

Turing now to FIG. 4 an introducer 112 according to an exemplary embodiment of the present disclosure is coupled to the cassette 28 via tubes 103 and 105 to deliver heated ablation fluid to the uterus and to return the ablation fluid from the uterus to the cassette. The tubes 103, 105 are coupled to the delivery and return lumens 102, 104, respectively, of the cassette 28, and also to ablation fluid delivery and return lumens (not shown in FIG. 4) within a sheath 113 of the introducer 112. The ablation fluid delivery and return lumens terminate at respective openings at or near a distal end 118 of the sheath 113 which openings are located within the uterus, when the introducer 112 is in an operative position.

The introducer 112 is further coupled to the cassette 28 via tube 111 through which a fluid sealant in accordance with the disclosure is delivered from the cassette 28 to the sheath 113. The tube 111 is coupled to the sealant lumen 110 of the cassette 28 and to a sealant delivery lumen not shown within the sheath 113 of the introducer 112. The sealant delivery lumen terminates at one or more openings between the fins of the cervical seal 126 which, when the introducer 112 is in an operative position, are located within the endocervical canal of the cervix.

The introducer 112 may optionally include a vision system to allow visualization of the operative area. Those of skill in the art will understand that the vision system may be substantially similar to the systems in conventional endoscopes (e.g., fiber optic or CCD-based systems, etc.). Alternatively, users may rely on the vision system of an endoscope or other instrument inserted through the introducer 112 as described below.

The introducer 112 includes a grip 114 (e.g., an ergonomic handle) coupled to the sheath 113 and a scope connector 116 for receiving a visualization device, such as an endoscope. (As also discussed below, scope connector 116 may also receive other devices to be introduced including catheters.) The grip 114 facilitates holding and manipulation of the introducer 112 with a single hand while the operator uses his free hand to interface with the console 4, adjust the visualization device, manipulate the patient's anatomy, and so forth. The scope connector 116 according to this embodiment is disposed on a proximal end of the introducer 112 and provides an attachment point for a visualization device (e.g., a hysteroscope, an endoscope, etc.) so that the visualization device may be passed distally through a visualization lumen in the introducer 112 and extended out of the distal end 118. Thus, the operator may visually monitor insertion of the introducer 112 into the uterus. In some embodiments, a single lumen may serve both as (a) the visualization lumen and ablation fluid delivery lumen or (b) the visualization lumen and ablation fluid return lumen.

The scope connector 116 may comprise an optional locking ring 117 and a scope adapter 120 which allow the introducer 112 to be adjusted to accommodate visualization devices of varying lengths. The visualization device is inserted into the proximal end of the introducer 112 through the scope connector 116 and locked thereto using the locking ring 117. The user then depresses the scope adapter 120 releasing the scope adapter 120 from a current locking aperture and allowing the scope connector 116 to slide proximally out of or distally into the introducer 112.

The grip 114 may further include a tenaculum stabilizer 122. For example, during the ablation procedure, a tenaculum may be employed around the cervix to enhance the seal of the cervix around the sheath 113 of the introducer 112. A tenaculum that has been clamped around the cervix may then be coupled to the introducer 112 to ensure that the introducer 112 remains at a desired position within the uterus and is not inadvertently withdrawn therefrom. A portion of the tenaculum is passed over the tenaculum stabilizer 122 preventing movement of the sheath 113 proximally relative to the tenaculum. The tenaculum stabilizer 122 is moved to a proximal-most position permitted by the tenaculum. Specifically, in an exemplary embodiment, the tenaculum stabilizer 122 includes a fin slidably mounted on a rail 124 formed on the grip 114. The fin includes a hook which may receive finger grips or a crossbar of a tenaculum as would be understood by those skilled in the art. When the tenaculum is coupled to the tenaculum stabilizer 122, the operator selects a tension to be applied between the tenaculum and the introducer 112 by moving the fin along the rail 124. A positioning mechanism (e.g., ratchet, latch, clip, etc.) may be used to maintain a position of the fin relative to the rail 124, as would be understood by those skilled in the art. Further information regarding a tenaculum stabilizer 122 like that shown and its operation can be found, for example, in Pub. No. 2009/0069796 to Oskin, which is hereby incorporated by reference.

The introducer 112 further includes a cervical seal 126 separated from a distal end 118 of the sheath 113 by a distance selected to ensure that, when the distal end of the sheath 113 is in a desired position within the uterus, the seal 126 is located within the cervix. When the distal end 118 of the introducer 112 is introduced into the uterus, the elasticity of the cervix provides a substantially fluid-tight seal around the sheath 113. However, to minimize the risk of ablation fluid escaping through the endocervical canal to damage non-targeted tissue, the fluid-tight seal may be enhanced/maintained using the cervical seal 126, which may comprise a plurality of flexible sealing members extending around the sheath. In the exemplary embodiment shown, the cervical seal 126 is formed as a series of flexible fins 226 encircling the sheath 113, which may be formed from an elastic material such as silicone, polyurethane or various other elastomers known in the art. Although twelve (12) fins 226 are shown, clearly any suitable number of fins may be employed include 1, 2, 3, 4, 5, 6, 7, 8, 9, 10, 11, 12, 13, 14, 15, 16, 17, 18 or more fins.

To further enhance the seal, a fluid sealant is delivered from the sealant lumen 110 of the cassette 28 via tube 111 into a sealant delivery lumen not shown within the sheath 113 of the introducer 112. The sealant delivery lumen terminates at one or more openings between the fins 226 of the cervical seal 126. As indicated above, by introducing a suitable thermoresponsive fluid sealant into the body at a temperature below body temperature and by allowing the composition to equilibrate with the temperature of the body, the viscosity of the fluid sealant increases dramatically, creating a tight seal.

Figure 5A:
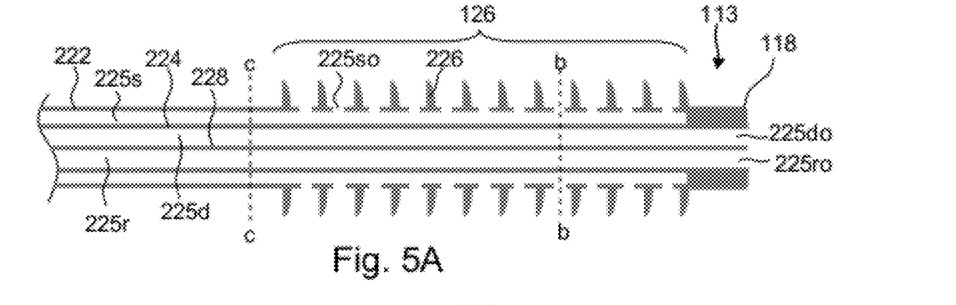
FIG. 5A is a cross-sectional view of an exemplary embodiment of a distal end of an introducer sheath according to the present disclosure.
Figure 5B:
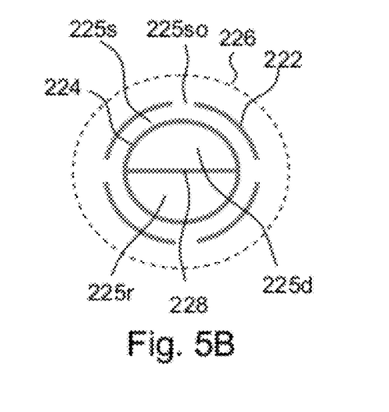
FIG. 5B is a cross-sectional view of the introducer sheath shown in FIG. 5A, taken along line b-b.
Figure 5C:
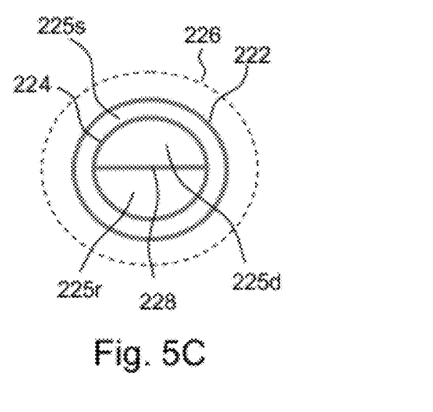
FIG. 5C is a cross-sectional view of the introducer sheath shown in FIG. 5A, taken along line c-c.

FIG. 5A is a detailed cross-sectional view of an exemplary embodiment of a distal end 118 of a sheath 113 like that shown in FIG. 4, including cervical seal 126. FIGS. 5B and 5C are cross-sectional views of such a sheath 113, taken along lines b-b and c-c, respectively, of FIG. 5A. These figures show the fins 226 of the cervical seal 126. These figures also show the multi-lumen nature of the sheath 113, which includes outer tubular portion 222, an inner tubular portion 224, between which is formed an annular sealant delivery lumen 225s. A 224 a divider portion 228 is provided within the inner tubular portion 224, forming a hemi-cylindrical ablation fluid delivery lumen 225d and a hemi-cylindrical ablation fluid return lumen 225r. The outer tubular portion 222 is provided with sealant openings 225so between fins 226 which allow fluid sealant to exit the sheath 113. The hemi-cylindrical ablation fluid delivery lumen 225d terminates at a semi-circular opening 225do at the distal end 118 of the sheath 113, and the hemi-cylindrical ablation fluid return lumen 225r terminates at a semi-circular opening 225ro at the distal end 118 of the sheath 113.

As indicated above, one of the hemi-cylindrical lumens 225d and 225r may accommodate a scope. In the embodiment of FIG. 5A, the ablation fluid delivery lumen 225d is in sealable communication (e.g., via a valve) with the scope connector 116 of FIG. 4. (Alternatively, the ablation fluid return lumen 225r, rather than the ablation fluid delivery lumen 225d, may be in sealable communication with the scope connector.)

Moreover, in certain embodiments, it is also desirable to block the fallopian tubes prior to circulation of the ablation fluid in the uterus. A sheath like that of FIG. 5A may be useful in this regard, as one of the hemi-cylindrical lumens 225d and 225r may be configured to deliver a catheter into the uterus prior to being used to deliver or return ablation fluid. For example, in the embodiment of FIG. 5A, the ablation fluid return lumen 225r may be in sealable communication (e.g., via valve) with a catheter port (not shown) associated with the scope connector 116 of FIG. 4. In this embodiment, a catheter disposed in the ablation fluid return lumen 225r may be used to deliver fluid sealant, while a scope disposed in the ablation fluid delivery lumen 225d may be used to locate each fallopian tube and guide the administration of the fluid sealant from the catheter. In an alternative embodiment, both the catheter and the scope may be inserted through a single lumen (e.g., through the return lumen 225r or the delivery lumen 225d).

Figure 6:
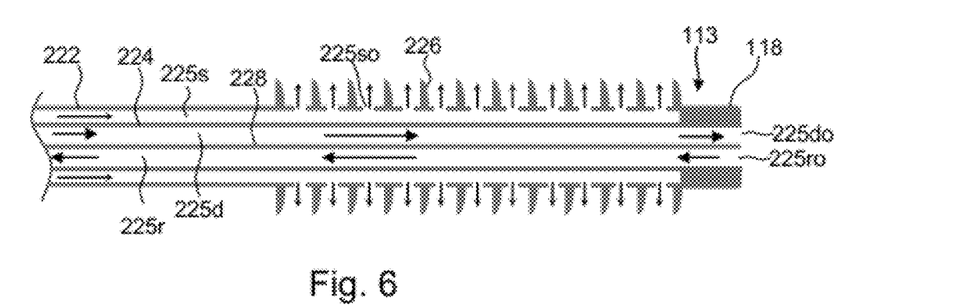
FIG. 6 is the cross-sectional view of FIG. 5A in which arrows have been added to indicate direction of flow.

FIG. 6 is like that of FIG. 5A, except that arrows are provided which show the following: (a) delivery of the fluid sealant through the sealant delivery lumen 225s and out of the sealant openings 225so to emerge from the sheath between the fins 226, (b) delivery of the heated ablation fluid through the ablation fluid delivery lumen 225d and out of the opening 225do at the distal end 118 of the sheath 113, and (c) return of the ablation fluid into the opening 225ro at the distal end 118 of the sheath 113 and through the ablation fluid return lumen 225r.

Figure 7:
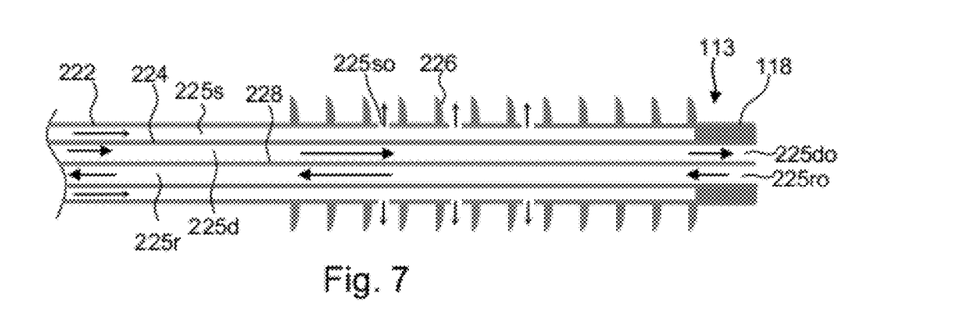
FIG. 7 is a cross-sectional view of another exemplary embodiment of a distal end of an introducer sheath according to the present disclosure in which arrows have been added to indicate direction of flow.

FIG. 7 is like that of FIG. 6, except that sealant openings 225so are provided between only three pairs of fins. Sealant openings 225so can clearly be provided between a single pair of fins or between any combination of fins.

Similarly FIG. 5B shows four sealant openings 225so between a given pair of fins (see line b-b of FIG. 5A). However one, two, three, five or more openings may be provided. In some embodiments, a sealant opening may in the form of a continuous slot that encircles the sheath.

Figure 8A:
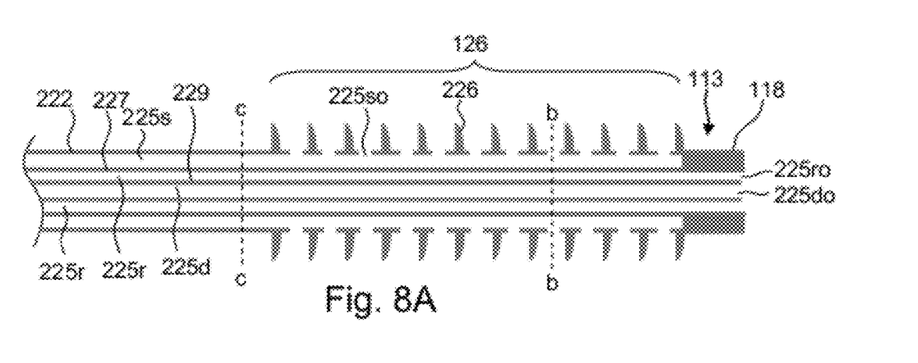
FIG. 8A is a cross-sectional view of another exemplary embodiment of a distal end of an introducer sheath according to the present disclosure.
Figure 8B:
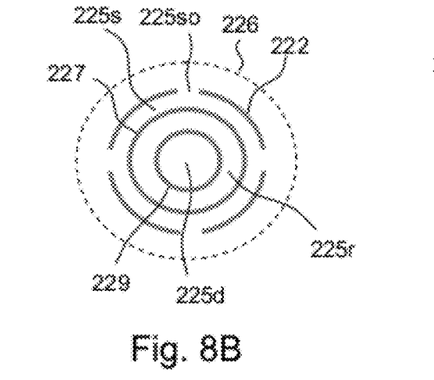
FIG. 8B is a cross-sectional view of the introducer sheath shown in FIG. 8A, taken along line b-b.
Figure 8C:
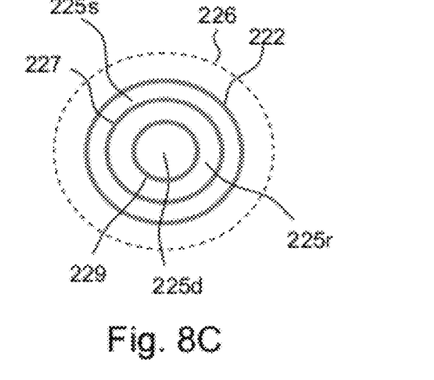
FIG. 8C is a cross-sectional view of the introducer sheath shown in FIG. 8A, taken along line c-c.

FIGS. 8A-8C are like FIGS. 5A-5C, except that the internal lumens of the sheath 113 are configured in a different fashion. In this regard, these figures show a multi-lumen sheath 113 having an outer tubular portion 222, an intermediate tubular portion 227 and an inner tubular portion 229, which form an annular sealant delivery lumen 225s, an annular ablation fluid return lumen 225r and a cylindrical ablation fluid delivery lumen 225d. As in FIG. 5B, the outer tubular portion 222 is provided with sealant openings 225so between fins 226. Moreover, the cylindrical ablation fluid delivery lumen 225d terminates at a circular opening 225do, at the distal end 118 of the sheath 113, while the annular ablation fluid return lumen 225r terminates at a ring-shaped opening 225ro at the distal end 118 of the sheath 113.

Moreover, analogous to FIGS. 5A-5C, in FIGS. 8A-8C, one of the lumens 225d, 225r may accommodate a scope, one of the lumens 225d, 225r may accommodate a catheter, one of the lumens 225d, 225r may accommodate a scope and the other may accommodate a catheter, or a single lumen (e.g., 225d) may accommodate both a scope and a catheter.

Figure 9:
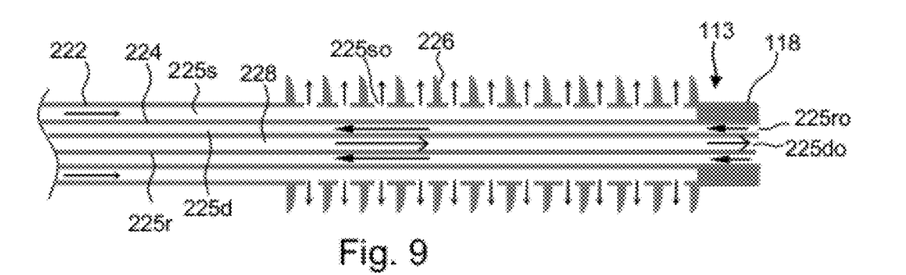
FIG. 9 is the cross-sectional view of FIG. 8A in which arrows have been added to indicate direction of flow.

In FIG. 9, various combinations of arrows are provided which show fluid flow associated with FIGS. 8A-8C, including the following: (a) delivery of the fluid sealant through the sealant delivery lumen 225s and out of the sealant openings 225 to emerge from the sheath between the fins 226, (b) delivery of the heated ablation fluid through the ablation fluid delivery lumen 225d and out of the circular opening 225do at the distal end 118 of the sheath 113, and (c) return of the ablation fluid into the ring-shaped opening 225ro at the distal end 118 of the sheath 113 and through the ablation fluid return lumen 225r.

Figure 10A:
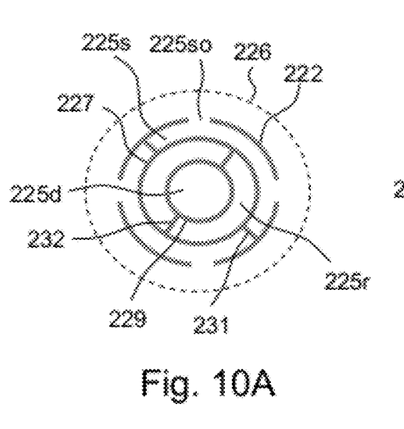
FIGS. 10A and 10B are alternative cross-sectional views of the introducer sheath shown in FIG. 8A, taken along lines b-b and c-c, respectively.
Figure 10B:
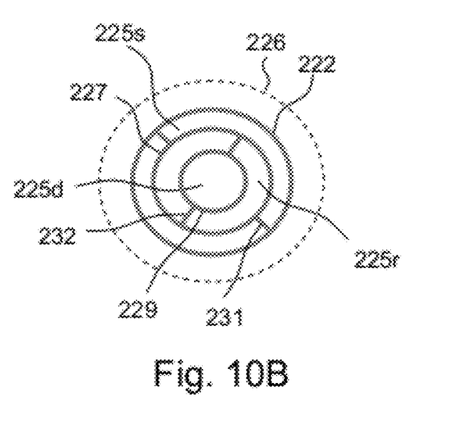

FIGS. 10A and 10B are like FIGS. 8B and 8C, except that stabilizing elements 231 are shown between outer tubular portion 222 and intermediate tubular portion 227 to maintain the spacing between tubular portions 222 and 227. These elements 231 may extend along the length of the sheath, creating two sealant delivery lumens 225s. In addition, stabilizing elements 232 are shown between intermediate tubular portion 227 and the inner tubular portion 229, which act to maintain the spacing between tubular portions 227 and 229. These elements 232 may extend along the length of the sheath, creating two ablation fluid return lumens 225r.

It is noted that, while ablation fluid and fluid sealant are shown flowing simultaneously in FIGS. 6, 7 and 9, in practice, the fluid sealant would be applied prior to the ablation fluid in order to provide a seal for the ablation fluid.

Various aspects of the invention of the invention relating to the above are enumerated in the following paragraphs:

Aspect 1. A method of conducting a fluid thermal ablation procedure in a human anatomy comprising a hollow organ and a natural or surgical passage between the hollow organ and the exterior of said human, said method comprising: (a) advancing an introducer comprising an elongate sheath into the hollow organ through the passage; (b) forming a seal between the sheath and the passage by introducing a thermoresponsive fluid sealant between the sheath and the passage, said thermoresponsive sealant fluid being introduced to the subject at an introduction temperature that differs from body temperature and increasing in viscosity between the introduction temperature and the body temperature of the subject; and (c) injecting heated fluid into the uterus through said sheath after said thermoresponsive sealant fluid undergoes said increase in viscosity.

Aspect 2. The method of aspect 1, wherein said human anatomy is a human female anatomy comprising a uterus, a vagina, and a cervix having an endocervical canal and wherein said method comprises (a) advancing the introducer into the uterus through the vagina and the endocervical canal of the cervix, (b) forming a seal between the sheath and the cervix by introducing the thermoresponsive fluid sealant between the sheath and the endocervical canal, and (c) injecting said heated fluid into the uterus through said sheath after said thermoresponsive sealant fluid undergoes said increase in viscosity.

Aspect 3. The method of aspect 2, wherein the female anatomy further comprises a fallopian tube and wherein an entrance to said fallopian tube is blocked by introducing said thermoresponsive fluid sealant into said entrance at said introduction temperature.

Aspect 4. The method of aspect 1, wherein said thermoresponsive sealant fluid is introduced to the subject at an introduction temperature of 35° C. or less.

Aspect 5. The method of aspect 4, wherein the thermoresponsive fluid sealant comprises a block copolymer comprising a plurality of polyoxyalkylene blocks.

Aspect 6. The method of aspect 1, wherein the introducer further comprises a plurality of flexible sealing members extending around the sheath and wherein the thermoresponsive fluid sealant is introduced between the flexible sealing members.

Aspect 7. The method of aspect 1, wherein said heated ablation fluid is introduced to the hollow organ through one or more delivery apertures at a distal end of said sheath and wherein ablation fluid is withdrawn from the hollow organ through one or more return apertures at the distal end of said sheath.

Aspect 8. An introducer comprising an elongate sheath having a distal end which, when in an operative position, is received within a hollow organ of a subject such that the distal end of the sheath lies within the hollow organ, said sheath comprising (a) an ablation fluid delivery lumen introducing heated ablation fluid to the hollow organ, (b) an ablation fluid return lumen withdrawing cooled ablation fluid from the hollow organ and (c) a fluid sealant delivery lumen introducing fluid sealant from at least one sealant aperture on a lateral surface of said sheath.

Aspect 9. The introducer of aspect 8, wherein the introducer comprises a plurality of flexible sealing members that extend around the sheath and wherein said sealant aperture is positioned between said sealing members.

Aspect 10. The introducer of aspect 8, wherein the hollow organ is a human female uterus, and wherein said sealant aperture is separated from the distal end of the sheath by a distance that ensures that, when the sheath is in said operative position after being inserted through a vagina and cervix of a subject, the aperture is located within an endocervical canal of the subject.

Aspect 11. The introducer of aspect 10, wherein the introducer comprises a plurality of flexible sealing members that extend around the sheath, wherein said sealant aperture is positioned between said flexible sealing members, and wherein when the sheath is in said operative position, the flexible sealing members are located within the endocervical canal of the subject.

Aspect 12. The introducer of aspect 8, wherein the ablation fluid delivery lumen is in the form of hemi-cylindrical lumen, wherein the ablation fluid return lumen is in the form of hemi-cylindrical lumen, and wherein the fluid sealant delivery lumen is in the form of an annular lumen surrounding the ablation fluid delivery lumen and the ablation fluid return lumen.

Aspect 13. The introducer of aspect 8, wherein the ablation fluid delivery and return lumens terminate at the distal end of the sheath.

Aspect 14. The introducer of aspect 8, wherein said fluid sealant is a thermoresponsive sealant fluid that undergoes an increase in viscosity between an introduction temperature of 35° C. or less and the body temperature of the subject.

Aspect 15. A cassette for a heated fluid ablation system, comprising: a fluid chamber containing a thermoresponsive fluid sealant; a fluid sealant delivery lumen delivering the fluid sealant from the cassette; and a first pump drive mechanism pumping the fluid sealant composition out of the fluid chamber via the fluid sealant delivery lumen.

Aspect 16. The cassette of aspect 15, wherein the first pump drive mechanism is a plunger.

Aspect 17. The cassette of aspect 16, wherein the fluid chamber is a syringe pump syringe.

Aspect 18. The cassette of aspect 15, comprising a fluid supply lumen receiving an ablation fluid from an external fluid source; an ablation fluid delivery lumen delivering the ablation fluid from the cassette; a second pump drive mechanism pumping the ablation fluid out of the cassette via the ablation fluid delivery lumen.

Aspect 19. The cassette of aspect 18, wherein the second pump drive mechanism is an impeller.

Aspect 20. The cassette of aspect 15, wherein the thermoresponsive fluid sealant comprises a block copolymer comprising a plurality of polyoxyalkylene blocks.

Aspect 21. A kit comprising (a) a thermoresponsive fluid sealant in a container and (b) instructions regarding the use of the thermoresponsive fluid sealant in conjunction with a heated fluid ablation procedure.

Aspect 22. The kit of aspect 21, wherein the container is a syringe pump syringe.

Aspect 23. The kit of aspect 21, wherein thermoresponsive fluid sealant comprises a reverse thermosensitive polymer that comprises polyoxyalkylene block copolymer.

Aspect 24. The kit of aspect 21, wherein said heated fluid ablation procedure is an endometrial ablation procedure.

Although various embodiments are specifically illustrated and described herein, it will be appreciated that modifications and variations of the present disclosure are covered by the above teachings and are within the purview of the appended claims without departing from the spirit and intended scope of the disclosure.

The invention claimed is:

1. A cassette for a heated fluid ablation system, comprising: a fluid chamber containing a thermoresponsive fluid sealant; a fluid sealant delivery lumen delivering the fluid sealant from the cassette; a first pump drive mechanism pumping the fluid sealant composition out of the fluid chamber via the fluid sealant delivery lumen; a heating chamber comprising a heating element configured to heat ablation fluid in the heating chamber; an ablation fluid delivery lumen in fluid communication with the heating chamber through which ablation fluid from the heating chamber is delivered from the cassette; an ablation fluid return lumen in fluid communication with the heating chamber though which returned ablation fluid is received by the cassette and returned to the heating chamber; and a second pump drive mechanism pumping the ablation fluid out of the cassette via the ablation fluid delivery lumen.

2. The cassette of claim 1, wherein the first pump drive mechanism is a plunger.

3. The cassette of claim 2, wherein the fluid chamber is a syringe pump syringe.

4. The cassette of claim 1, further comprising a fluid supply lumen receiving the ablation fluid from an external fluid source.

5. The cassette of claim 1, wherein the second pump drive mechanism is an impeller.

6. The cassette of claim 1, wherein the thermoresponsive fluid sealant comprises a block copolymer comprising a plurality of polyoxyalkylene blocks.

7. The cassette of claim 1, wherein the thermoresponsive fluid sealant undergoes an increase in viscosity when warmed to body temperature from a temperature below body temperature.

8. The cassette of claim 1, further comprising a cold-pack in which a seal is broken to combine contents of separate containers which react and absorb energy, creating a cooling effect, said cold pack being in or adjacent to the fluid chamber and being configured to cool the thermoresponsive fluid sealant within the fluid chamber.

9. The cassette of claim 7, further comprising a cold-pack in which a seal is broken to combine contents of separate containers which react and absorb energy, creating a cooling effect, said cold pack being in or adjacent to the fluid chamber and being configured to cool the thermoresponsive fluid sealant within the fluid chamber.

10. The cassette of claim 1, wherein the thermoresponsive fluid sealant comprises a reverse thermosensitive polymer that comprises polyoxyalkylene block copolymer.

11. The cassette of claim 7, wherein the thermoresponsive fluid sealant comprises a reverse thermosensitive polymer that comprises polyoxyalkylene block copolymer.

12. The cassette of claim 9, wherein the thermoresponsive fluid sealant comprises a reverse thermosensitive polymer that comprises polyoxyalkylene block copolymer.

13. The cassette of claim 8, wherein the thermoresponsive fluid sealant comprises a reverse thermosensitive polymer that comprises polyoxyalkylene block copolymer.

* * * * *